United States Patent [19]
Taylor et al.

[11] Patent Number: 6,083,257
[45] Date of Patent: Jul. 4, 2000

[54] BRAIDED STENT

[75] Inventors: Alistair Stewart Taylor; Peter William Stratford; Yiannakis Petrou Yianni; Matthew John Woodroffe, all of Surrey, United Kingdom

[73] Assignee: Biocompatibles Limited, Surrey, United Kingdom

[21] Appl. No.: 09/011,523
[22] PCT Filed: Nov. 1, 1996
[86] PCT No.: PCT/GB96/02689
  § 371 Date: Apr. 28, 1998
  § 102(e) Date: Apr. 28, 1998
[87] PCT Pub. No.: WO97/16133
  PCT Pub. Date: May 9, 1997

[30]     Foreign Application Priority Data

Nov. 1, 1995  [GB]  United Kingdom ................... 9522332

[51] Int. Cl.$^7$ ........................................... A61F 2/06
[52] U.S. Cl. ................................... 623/1; 623/12
[58] Field of Search ............................ 623/1, 12

[56]            References Cited
          U.S. PATENT DOCUMENTS

| | | | |
|---|---|---|---|
| 3,479,670 | 11/1969 | Medell | 623/1 |
| 5,061,275 | 10/1991 | Wallsten et al. | 623/1 |
| 5,282,846 | 2/1994 | Schmitt | 623/1 |
| 5,653,746 | 8/1997 | Schmitt | 623/1 |
| 5,653,747 | 8/1997 | Dereume | 623/1 |
| 5,849,037 | 12/1998 | Frid | 623/1 |
| 5,851,217 | 12/1998 | Wolff et al. | 623/1 |

*Primary Examiner*—David H. Willse
*Assistant Examiner*—Suzette J. Jackson
*Attorney, Agent, or Firm*—Sughrue, Mion, Zinn, Macpeak & Seas, PLLC

[57]            ABSTRACT

A braided stent (1) for transluminal implantation in body lumens is self-expanding and has a radial expanded configuration in which the angle α between filaments is acute. Some or all of filaments (6,7) are welded together in pairs at each end (4,5) of the stent to provide beads (8), thereby strengthening the stent and assisting its deployment from a delivery device. The stent is preferably completely coated using a biocompatible polymeric coating, said polymer preferably having pendant phosphoryl choline groups. A method of making the stent by braiding and welding is described as well as a delivery device for deploying the device.

19 Claims, 4 Drawing Sheets

BRAIDED STENT

BACKGROUND OF THE INVENTION

1. Field of the Invention

The present invention relates to an implantable stent for transluminal implantation in body lumen, especially found in peripheral and coronary blood vessels, but also for use in bile ducts, urethras or ileums.

2. Description of the Related Art

There are several designs of stents, permanently implantable devices, for transluminal insertion into blood vessels and other lumen to prevent or reverse occlusion thereof. There are three basic categories of device, namely heat-expandable devices, balloon-expandable devices and self-expanding devices. The present invention is concerned with self-expanding devices with an optional heat expanding capability, that is which are inserted into the body lumen in a radially compressed condition and which are mechanically biased towards a radially expanded position. Upon being released in the blood vessel at the desired position, the stent expands radially exerting outwardly directed pressure upon the inner surface of the wall of the body lumen in which it is positioned.

One such expanding device which is commercially available is the so-called Wallstent. The device is described in WO-A-83/03752. It consists of two sets of counter-rotating helical filaments of metallic wire which are braided together in a one over/one under pattern. Although it is suggested in the above mentioned patent specification that the axially directed angle α between filaments at crossover points can be acute, it is preferably at least 900 and more preferably 1000 or more, which the author indicates is essential to provide adequate radial strength in use such that the stent remains in its radially expanded condition.

There are difficulties with the braided stent of this type. One difficulty is that with a high angle α the change in axial length between the radially expanded and the radially compressed condition is generally high. One way of overcoming that problem has been described, in WO-A-92/00043, which describes a stent consisting of two co-axial and slidably connected braided stent segments. In the radially compressed condition the stent segments are in a telescoped condition such that the stent portions overlap with one another over a higher proportion of their respective lengths. Upon deployment each segment contracts in the axial direction, such that the length of overlap between the sections is decreased whilst retaining the same distance between the stent ends. This arrangement, however, adds complexity to the manufacture and deployment and it is difficult to allow for the mutual sliding between stent segments without snagging.

Another difficulty with braided stents in general is the tendency of the filaments at the end of the stent to unravel and splay outwards before or after deployment. This tendency makes the stent difficult to handle and the splayed ends can damage the inside wall of the body vessel in which the stent is deployed. In WO-A-83/03752, it is suggested that the filaments may be joined to one another at the end of the stent. However, as explained in a later specification by Wallsten et al in U.S. Pat. No. 5,061,275, for stents with a high angle α between counter-rotating filaments, that this rigidifies the ends of the prosthesis. This makes it difficult to compress the stent into its radially compressed condition. It is also said to accentuate the risk of penetration of the ends of the filaments through the wall of the vessel.

In DE-A-4,240,177 & U.S. Pat. No. 5,503,636, a braided stent is formed from wire having a rectangular cross-section. The wires are rigidly connected to one another at the crossover points and at the ends of the stent, by sheathing the filaments with a plastics material, applied whilst the stent is held in its radially expanded condition, in which the angle α is obtuse.

An early disclosure of a dilator for body vessels appears in GB-A-1205743. This consists of counter-rotating helices which may be braided or may not be braided but joined at the crossover points. Where the dilator is made from counter rotating wire helices, it is suggested that the ends of the metal wires may be joined by swaging or welding. The angle between filaments at the crossover is said to be preferably in the range 45° to 60°, which is said to give a desired low ratio of axial extension to change in diameter (i.e. length change upon change in radius).

Another example of a braided stent is described in EP-A-0,183,372. The filaments in this publication are formed preferably of plastics material and the device generally has a warp thread extending parallel to the axis of the stent. The warp filament may be formed of shrinkable plastics to allow expansion of the stent insitu to its radially expanded condition.

SUMMARY OF THE INVENTION

A new radially self-expanding stent according to a first aspect of the invention adapted for implantation in a body passage comprises first and second sets of mutually counter-rotating metallic filaments which are braided together and define a tubular stent body having two ends which is mechanically biased towards a first radially expanded configuration in which it is unconstrained by externally applied forces and can be retained in a second radially compressed configuration, in which in the said first configuration the angle α between the filaments at a crossover point at the mid point of the stent is less than 90° and in which some or all of the filaments at the ends of the body are fixed together in pairs each consisting of counter-rotating filaments such that the angle at which the filaments are fixed is within the range α−10 to α+10 by a bead of metal which has a diameter of at least 1.2 times the mean diameter of an individual filament.

DETAILED DESCRIPTION OF THE INVENTION

Although the ends of the filaments may be fixed together by other means, for instance by swaging as disclosed in GB-A-1,205,743, mentioned above, it is most convenient for the fixing to be by welding. Although the welding can be by resistance welding and/or by pressure, it is preferred for heat to be used, generally by plasma welding. Preferably the welding softens the metal such that it forms a globule before resolidifying to form a bead.

For some embodiments and applications it may be adequate to weld some but not all of the filament ends. For instance it may be convenient to weld every third pair of counter-rotating filaments at the end of one or both ends of the stent body. Preferably at least every other pair is welded at both ends, more preferably every pair at one, or preferably, both ends.

Preferably no filler wire is used in the welding although it may, for some purposes, be useful to include filler wire, for instance where the filler has different, usually greater, radiopacity than the material from which the metal filaments are made. The formation of a bead and/or the use of high radiopacity filler material at the join enables the ends of the stent to be made more radiopaque (to X-rays transmitted perpendicular to the axis) than the body of the stent between the ends. This assists in visualisation of the stent during an operation.

A bead generally has a diameter of at least 1.2 times that of the diameter of the filament, for instance at least 1.5 times or as much as or more than 2 times the diameter. The diameter of the bead is usually no more than 3, preferably less than 2.5, times the diameter of the filament. We have found that it assists retention of the stent on a delivery device and its delivery from that device if the bead's periphery extends outwardly beyond the periphery of the stent as defined by the filament surfaces, preferably on the inner and outer wall. This results in the bead providing shoulders on either or both the inner and outer walls which can provide an axially directed surface against which a corresponding axially directed surface on a movable component of a delivery device can bear to impose motion of the stent relative to other components of the delivery device. Preferably each bead provides shoulders in forward and rearward axial direction. The shape of the resolidified bead at least on the outer wall of the stent is generally rounded, for instance approximately spherical, and this provides a smooth external stent surface to minimise damage to the inside wall of the vessel in which the stent is implanted.

Where the ends of the filaments are joined together using a treatment involving the use of high temperatures, this may change the properties of the material of the filament in the portion subjected to the increased temperature, generally at the end portions and especially where the filaments are made of steel. Since this may affect the mechanical properties of the wire such that a difference is imposed in properties between the ends and the body between the ends, it may be desirable to anneal the stent before or after the welding, for instance by subjecting the central portion, usually the entire stent, to heat treatment. For instance where the metal from which the filaments are made is a high cobalt stainless steel, welding is generally carried out at the temperature of 1480° C. It is suitable for annealing to be conducted by subjecting the stent after the welding operation to heat treatment at the annealing temperature for the metal for a sufficient period. For high cobalt steel, for instance, the annealing is carried out at a temperature in the range 510 to 530° C., for instance around 520° C. for a period of at least 2 hours, preferably about 3 hours.

The first radially expanded diameter is the diameter adopted by the stent when no externally directed force is exerted upon it, that is when it expands in air. This diameter is somewhat greater than the internal diameter of the lumen into which stent is to be implanted since this results in the stent exerting a continuous outwardly directed force on the internal wall of the body lumen in which it is located. In this fully unloaded conformation the angle α between filaments is less than 90°. Generally it is less than 85°, preferably in the range 65–85°, most preferably in the range 70 to 80°.

Preferably the angle between the filaments at a crossover point at the mid point of the stent in situ when implanted in a body lumen is in the range 60–90°, preferably in the range 65–75°.

Preferably the angle at which the filaments are fixed at the ends of the stent is less than a. The angle is preferably in the range α–5 to α+5, more preferably α–5 to α.

The metallic stent is generally provided with a biocompatible coating, in order to minimise adverse interaction with the walls of the body vessel and/or with the liquid, usually blood, flowing through the vessel. The coating is preferably a polymeric material, which is generally provided by applying to the stent a solution or dispersion of preformed polymer in a solvent and removing the solvent. Non-polymeric coating materials may alternatively be used. Suitable coating materials, for instance polymers, may be polytetrafluoroethylene or silicone rubbers, or polyurethanes which are known to be biocompatible. Preferably however the polymer has zwitterionic pendant groups, generally ammonium phosphate ester groups, for instance phosphoryl choline groups or analogues thereof. Examples of suitable polymers are described in our earlier application number WO-A-93/01221. Particularly suitable polymers described in that specification are those which are cross-linkable after coating, since these remain stably adhered to the surface. We have described other suitable biocompatible coating polymers which may be used in WO-A-94/16748, WO-A-94/16749 and WO-A-93/15775. Polymers as described in those specifications are hemo-compatible as well as generally biocompatible and, in addition, are lubricious. It is important to ensure that the metallic surfaces of the stent are completely coated in order to minimise unfavourable interactions, for instance with blood, which might lead to thrombosis. Although it may be possible to avoid the exposure to blood or metal surfaces at the crossover points, on the mutually contacting portions of the filaments, by sheathing the entire crossover points and hence fixing the filament to one another, as described in DE-A-4,240,177 (mentioned above), it is preferred that the crossover points along the body of the stent should not be fixed to one another but should be allowed to move, for instance slide relative to one another. It is thus preferred for the coating to cover entirely the wires even at the crossover points. This can be achieved by suitable selection of coating conditions, such as coating solution viscosity, coating technique and/or solvent removal step. A preferred technique is described in the worked example set out below.

It is preferred that each filament of the stent should execute at least one full turn of the helix. If the filaments execute less than a full turn, even with the joining of the ends of the filaments, the stent may be relatively unstable. Preferably each filament executes at least 1.2 turns, though generally less than three turns, preferably less than two turns. It is preferred that the stent be formed from at least 4, more preferably at least 8 and most preferably at least 12 filaments in each direction. The number of filaments depends at least in part upon the diameter of each filament as well as the desired diameter and the desired size of the openings between the filaments of the stent in its radially expanded and contracted condition. The number of filaments and their diameter affects the flexibility of the stent in its radially contracted condition during delivery and it is preferred for the stent in that condition to be as flexible as possible. Generally the number of filaments in each direction is less than 32, more preferably from 24 downwards.

The filaments may be made from circular section wire. It may, alternatively be advantageous for rectangular section wire to be used, for instance as described in DE-A-4240177 and in the early Wallsten patent WO-A-83/03752. The use of flat (rectangular section wire) may provide optimum radial strength characteristics whilst minimising the overall thickness of the stent, especially at the crossover points, thereby minimising any interference of the liquid flow in the body passageway. The area of contact between wires at the crossover points is maximised by the use of flat wire which increases the amount of friction between the wires upon relative movement, for instance during any changes in radius. This should increase the resistance of the expanded stent to radial contraction in use although it may be disadvantageous to increase this area during delivery. The use of oval wire (with the smaller dimension being arranged substantially radially with respect to the stent axis) may provide a particularly advantageous combination of strength whilst minimising the contact area at crossover points.

The braiding is usually in a one over-one under pattern although other patterns such as one under-two over or two under-two over could be used.

The thickness of the filaments depends upon the desired final diameter (open diameter) of the stent. Wire having a diameter of 0.04 mm upwards, for instance up to 0.20 mm may be used. Wire with diameters at the lower end of the range would generally be used for making stents for use in small blood vessels, for instance in coronary arteries, where the diameters of the stents is generally in the range 0.5 mm up to 4.0 mm (fully radially expanded diameter). Larger stents may be used in peripheral blood vessels, aortic aneurisms or in stents for use in urological passageways, the oesophagus and in the bile duct, where the stent may have a diameter up to about 30 mm.

The length of the stent in the fully unloaded conformation may be in the range 10 to 500 mm. The length depends on the intended application of the stent. For instance in peripheral arteries the stent may have a length at the upper end of the range, for instance in the range 100 to 300 mm. For coronary arteries, the length may be in the range 10 to 50 mm.

For most of the passageways, the diameter of the stents in the first radially expanded conformation is substantially constant along the length of the stent. The stent may flare or have a reduced diameter towards the end portion, in some instances. However, for an insertion into some body passages it is preferred for the diameter, that is the cross-sectional area, to vary along the length of the stent. For instance it may reduce migration of a device by providing it with a varying diameter along its length such that increased diameter sections and/or reduced diameter sections locate at and interact with, respectively, increased diameter body passageways (for instance openings into a higher volume organ) or reduced diameter sections, for instance at a sphincter. Such varying diameter portions may be provided by use of an appropriate braiding mandrel, or alternatively by a post-braiding heat treatment, welding or by provision of shaped restraining means such as non-helical filaments etc. Alternatively two or more stent segments may be fitted together for instance by welding two independently formed sections having the desired shape. One particular application of a varying diameter stent is a stent for use in urological passageways, for instance to overcome benign prostatic hyperplasia.

The filaments from which the braided stents are made are formed of a metal, for instance surgical steel, usually of a type having good elastic properties, for instance a high cobalt stainless steel. These such materials give a stent having good self-expanding capability.

In addition to the self-expanding capability of the stent, it may be provided with a temperature dependent mechanical characteristic which allows a mechanical property of the stent to be changed by heating the stent from a temperature below transition temperature to above transition temperature. Thus some or all of the filaments may be formed from a shape memory alloy material such as nitinol. In such cases, in the stent prior to implantation, the stent is at a temperature below the transition temperature at which the metal changes from the martensitic structure to the austenitic structure. The filaments are adapted such that a transition from below the transition temperature to above the transition temperature will result in the stent either adopting a radially further expanded configuration or, preferably, retaining the same shape but having an increased resistance to radial collapsing under inwardly exerted pressure, due to the greater hardness of the metal at the higher temperature.

According to a further aspect of the invention there is provided a radially self-expanding stent adapted for implantation in a body passage which comprises first and second sets of mutually counter-rotating metallic filaments which are braided and define a generally tubular stent body having two ends which is mechanically biased towards a first radially expanded configuration in which it is unconstrained by externally applied forces and can be retained in a second radially compressed configuration and in which the helically arranged filaments include filaments which are formed of an alloy which can change shape and/or hardness when heated from a temperature below a transition temperature of the alloy to a temperature above the transition temperature, in which the stent is below the transition temperature of the alloy and the shape memory alloy filaments of the stent are adapted to be changeable, when the stent is heated to a temperature higher than the transition temperature, either to a shape where the stent adopts a third maximal radially expanded configuration in which the diameter of the stent is greater than in a said first configuration or to an increased hardness such that the resistance of the stent to radial compression is increased.

The stent of the second aspect of the invention preferably has the features of the stent of the first aspect. This it preferably has welded ends and preferably has an angle α less than 90° in the maximally expanded condition.

The alloy which is used in this aspect of the invention preferably has a transition temperature in the range 30 to 45° C., more preferably around body temperature. It can be heated either by contact with a heater or, where the transition temperature is about 35 to 40° C., by being implanted in the patient where it will warm up from room temperature to body temperature, i.e. to the transition temperature. Such alloys are known. Where such an alloy is used it may be used to form all or only some of the filaments of the stent. Where the filaments of such an alloy are used and are desired to be welded, a counter-rotating pair of filaments of the same material are preferably welded together. Where there are pairs of one type of metal to be welded and pairs of another type of metal to be welded, the welding may be carried out in two stages, especially where the optimum welding conditions for the materials are different.

When it is used, the stent of the second aspect of the invention is inserted into the body lumen in its radially compressed configuration and is allowed to self-expand within the vessel. Subsequently the stent is heated to a temperature above a transition temperature of the alloy thereby causing the stent to assume a radially further expanded configuration and/or exert a greater outwardly directed force on the internal wall of the body lumen and/or resist radial compression to a greater degree. The invention thus provides an added degree of control as compared to a standard self-expanding stent upon the radial strength of the stent and/or the pressure it exerts on the vessel wall.

According to the invention there is also provided a method of making the new stents by braiding filaments over a first mandrel to make an elongate precursor, severing a pre-selected length from the precursor, placing the severed portion onto a second mandrel which has a diameter which is within the range (0.8 to 1.25)×d (where d is the diameter of the stent in its radially expanded condition) such that one end of the braided portion extends beyond the end of the second mandrel and in the method the protruding ends of at least some of the filaments are joined to each other in counter-rotating pairs, whereby each pair of joined counter-rotating filaments is joined by a bead of metal having a diameter of at least 1.2 times the mean diameter of the individual filaments.

The braiding is carried out on a standard braiding rig which generally provides a continuous length of braided tubing. The filaments are wound on to the bobbins and the process conditions, for instance in terms of the tension in the filaments, the diameter of the bobbin and the braiding angle during the braiding process determined by the haul off speed are selected using common general knowledge of the person skilled in the art of braiding, to produce a product having the desired characteristics in terms of expandability, radial strength and angle. It has been found that increasing the tension in the filaments during the braiding step, for instance to close to a maximum value above which the filaments would break, provides a stent having good radial strength and which does not collapse upon axial bending of the stent.

After the braid has been formed, it is subjected to any heat treatment and to welding. Whilst these steps may be carried out in either order, it may be convenient to subject an elongate stent precursor, which will be used to form a number of stents, to heat treatment prior to welding, which involves cutting the elongate precursor into stent length sections. It is preferred for heat treatment to be carried out in an inert gas environment for instance of argon gas.

The stent could also be included in a graft used to replace damaged blood vessels (aneurisms). For instance a stent according to the invention could be surrounded by a sleeve, of a porous or non-porous, elastic or inelastic, material. Alternatively a sleeve could include one stent at each end, secured for instance by suturing or other means, to the stent. The stent can be sterilised before use using standard techniques.

The joining step of the process is generally by welding the ends together, preferably by using a filler-free technique. As mentioned above, the welding generally creates a globule of molten metal which resolidifies to form the bead. It is most convenient for all the filaments which are required to be welded at one end of the stent to be joined in their respective pairs simultaneously and, in a separate step, for all the filaments which are required to be welded at the other end of the stent to be joined in their respective pairs simultaneously.

Where the ends of the filaments are joined by welding, this generally means that the filaments in the region of the stent adjacent to each end have been subjected to a higher temperature than the filaments in the body of the stent between the two ends. This can result in a change in the hardness of the metal adjacent the ends of the stent which may be undesirable. It may be advantageous, therefore, to subject the entire stent to an annealing step such that the hardness of the metal throughout the stent is equalised. Annealing is, for instance, carried out by subjecting the previously unheated section of the stent or, more usually, the entire stent, to heat treatment at the annealing temperature. For high cobalt steel, for instance the annealing temperature is in the range 510 to 530, preferably around 600° C., for a period in the range 1 hour to 1 day usually at least 2 hours preferably in the range 3 to 4 hours. This annealing step does not generally further change the hardness of the end section. Alternatively the stent precursor can be annealed prior to the end joining step.

The elongate precursor is generally sufficiently long for it to be used to make several stents, for instance at least five. Portions of an appropriate length are severed from the elongate precursor, generally after securing the ends to prevent them immediately unravelling upon severance. For instance it is possible to weld the filaments at crossover points near to the end of the portion prior to severance, for instance by resistance welding in a ring around the precursor, generally at two positions, one on each side of the place where the precursor is to be severed.

The second mandrel on which the severed length of braided portion is mounted is generally specifically adapted for carrying out the step of joining the filament ends together. Generally it is provided with circumferentially arranged pockets at its end, in each of which-sits a pair of filaments to be joined together. The width of the pocket and its shape allows selection of an appropriate angle at which the filaments are to be joined. The length of filaments extending beyond the end of the mandrel generally affects the shape and size of the globule formed upon carrying out the welding step. It is preferred for a heat sink to be contacted with the filaments, for instance the mandrel itself or a ring of material provided outside the filaments around the ends of the mandrel. This heat sink also affects the shape and position of the bead of metal formed upon carrying out the welding step.

Where the final stent is to be coated with a biocompatible polymer, this coating is carried out at a final step, after the welding and any heat annealing. Preferably the entire stent is immersed in a coating liquid and is then drained. Subsequently the coating is dried to leave an adherent polymer coating. Usually the coating liquid is a solution or dispersion of polymer in a solvent and, in the drying step, solvent is removed by evaporation. As mentioned above, it is important for all surfaces of the filaments to be coated, including the surfaces which contact one another at the crossover points. In a preferred coating step of the invention, as a part of the drying step, an axially directed flow of gas is passed along the stent to which coating solution has been applied. This gas causes the solution to flow between the filaments at the crossover points, so as to provide an overall coating.

The stent can be delivered using conventional delivery devices for self-expanding stents generally by percutaneous transluminal techniques. The stent may be delivered from a delivery device comprising a pusher and an external sleeve. The stent is retained against the end of the pusher within the sleeve, so that the device can be inserted transluminally until the stent is in the desired location in the body passageway. The pusher can then be used to push the stent so that it moves distally relative to the sleeve and is extruded therefrom to be positioned in the body passageway at the desired location. Such devices are described, for instance, in U.S. Pat. No. 4,655,771 (Wallsten). In such a delivery device, the stent is held in its radially compressed configuration by being retained within the sleeve. It expands to its radially expanded configuration as it is extruded from the end of the sleeve.

An alternative delivery device is also described in U.S. Pat. No. 4,655,771, which is similar to the device described in GB-A1205743, in which the stent is held at each end such that the ends are pulled apart, thereby stretching the length axially and reducing the diameter. The stent can be delivered by moving the ends together and releasing them. This allows central deployment, that is deployment in which the central section of the stent expands whilst the ends are retained in the radially compressed configuration. This may allow the stent to be moved within the body passageway during deployment in both directions until the desired location is achieved. This is an improvement as compared to the device extruded from one end of a sleeve, which can be moved in one direction only during deployment.

A further device for deploying a self-expanding stent is described in EP-A-0408245. In this device means are provided for allowing the stent to be retracted back onto an external sleeve by providing an internal pusher which have a shoulder beyond the distal end of the stent with a proximally directed shoulder which bears against the distal end of the stent allowing the stent to be pushed back into the sleeve prior to complete delivery.

A further device for delivering a self-expanded stent has been described in U.S. Pat. No. 5,078,720. In this device the stent is retained in an annular space having a proximally directed opening and which is fixed to the end of a pusher. The stent can be positioned in a retrograde manner, that is released from the proximal end first, by moving the device having the annular space distally whilst providing relative movement of the stent by providing a proximally direct shoulder on an inner tube which moves relative to the device having the annular space. A centrally deploying device is described also in U.S. Pat. No. 5,201,757. In this device, each end section of the stent is retain within an annular space, with the compressed diameter being achieved by retention within the annular space, the stent bearing against the external wall of the space.

Wallsten has described an alternative device referred to as the "rolling membrane device", in which a membrane is folded over upon itself to provide a double wall sleeve within which the stent is retained. When the outer wall is moved proximally, the distal fold travels proximally, exposing the stent allowing radial expansion from the distal end.

U.S. Pat. No. 5,415,664 describes a method for retrograde delivery of a self-expanding stent.

The provision of a stent having welded ends, in which the beads by which the ends are welded have peripheries extending beyond the periphery defined generally by the filaments allows for a particularly convenient delivery device and method, as described herein below. The present invention includes apparatus comprising a combination of delivery device with stent mounted ready for delivery.

In a preferred aspect of the invention there is provided a combination of stent in its radially compressed configuration and delivery device in which the delivery device comprises an internal pusher tube comprising an inner guidewire lumen for receiving a guidewire, and an external sleeve, the sleeve and pusher defining there between an annular space, wherein the stent is surrounded along substantially its entire axial length by the sleeve and at least one end of the stent is retained in the annular space between the sleeve and pusher. The device comprises means for providing relative axial movement between the pusher and the sleeve, preferably such that the sleeve moves proximally (with respect to a component of the device held in an axially fixed position by the surgeon) whilst the pusher moves distally to an extent whereby the stent is extruded beyond the distal end of the sleeve for delivery.

Where the stent comprises beads which provide a shoulder, as defined above, the pusher is provided with corresponding axially directed surfaces which can cooperate with these shoulders to impose motion on the stent relative to the sleeve. These surfaces are generally provided as the walls of a circumferential groove in the outer wall of the pusher tube, the groove being of a suitable width and/or depth for receiving the beads. Alternatively the stent may be delivered from a device in which the sleeve and pusher provide differential levels of friction with the stent whereby when the sleeve and pusher are moved relative to one another, the stent stays substantially fixed relative to the components (usually the pusher) and slides relative to the other.

The delivery device may have means to allow central deployment of the stent, that is allowing for radial expansion of the stent in the central portion prior to release of the ends from the radially compressed state on the delivery device. Central deployment may be achieved by means as described in some of the above mentioned prior art specifications (as indicated).

Where the stent is deployed centrally, it is possible for the position of the stent to be readjusted prior to full deployment or alternatively to be removed from the vessel altogether. Where the distal end of the stent is released, only proximal readjustment of the stent is possible when the stent is partially deployed, otherwise the end could become embedded in the vessel wall and cause damage. Likewise, where the proximal end is fully delivered prior to the distal end, the position of the stent can be readjusted in a distal direction but not a proximal direction. The delivery device may allow for the stent to be retracted back into a sleeve after partial deployment, to allow for respositioning.

The present invention is illustrated further in the accompanying figures in which.

Figure 1:
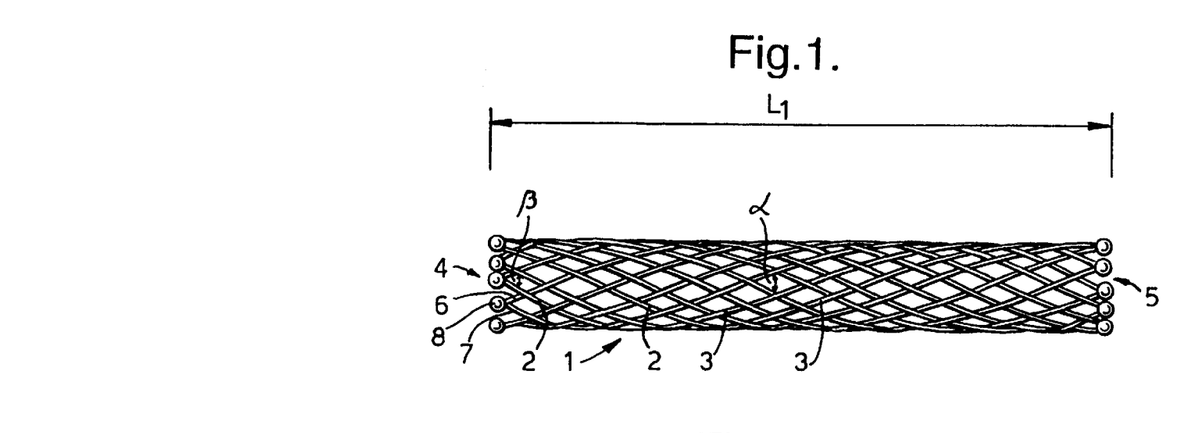
FIG. 1 is a side view of a stent according to the present invention in relaxed, radially expanded condition.
Figure 2:
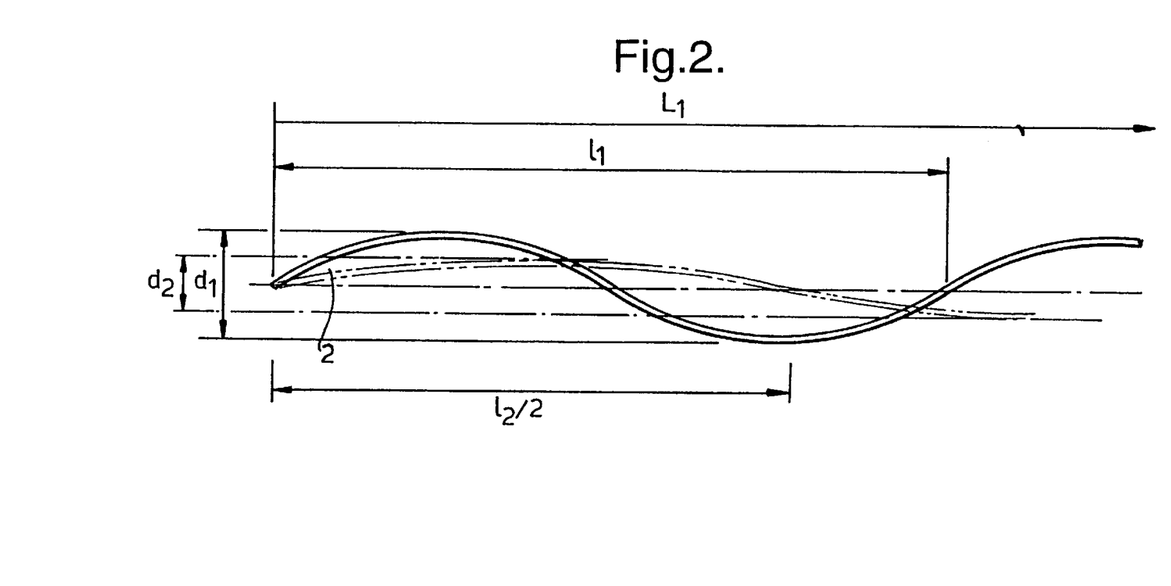
FIG. 2 shows the minimum path of one filament in the stent of a first aspect of the invention.

As shown in FIG. 1, a stent 1 is formed of ten wire filaments 2 arranged in right handed helices and ten filaments 3 arranged in left handed helices. The filaments are braided in a one over/one under pattern. The angle α between the filaments in the radially expanded (relaxed, unloaded) condition is generally in the range 60–90, in this embodiment in the range 68–72°. Each filament, as shown more clearly in FIG. 2 which is enlarged relative to FIG. 1 executes just over one complete turn (about 1¼ turns) within the length L of the stent. Each turn of the helix has a pitch of $l_1$. The diameter of the stent, and of each helix is $d_1$. In the radially compressed condition and axially extended condition, the length L increases to $L_2$, whilst the pitch of each helix increases from $l_1$ to $l_2$ and the diameter reduces from $d_1$ to $d_2$. The dotted line in FIG. 2 shows a portion of the filament 2 in its radially compressed state and indicates the length of one half of a turn of the helix as $l_2/2$.

Reverting to FIG. 1, at the ends 4 and 5 of the stent a pair of counter-rotating helices 6, 7 are connected together by an approximately spherical bead of metal 8 formed by fusing the wires 6 and 7. The angle $\beta$ on the tangential plane on the surface of the body between the filaments 6 and 7 is, in this embodiment, slightly lower than the angle $\alpha$ by about 5°. Alternatively it may be higher than or about the same as the angle $\alpha$. With the angle $\beta$ selected as illustrated, in the fully unloaded condition, the ends of the stent do not flare, or do not flare to a disadvantageous degree.

The stent illustrated in FIG. 1 is, for instance, suitable for implanting in a coronary artery. The diameter $d_1$ is in the range 2.5–4.0 mm. The diameter $d_2$ of the stent, in its axially compressed condition is generally at least ⅓ less than diameter $d_1$, and for instance in the range 0.5 to 2.0 mm. The wire used to form the filaments has a circular section and a diameter of 0.09 mm. The wire is formed from a high cobalt stainless steel. The beads 8 include no filler material but consist only of the material from which the wire of the filaments is formed. The blobs generally have a diameter in the range 0.18 to 0.22 mm. When visualised using X-rays, the end portions of the stent including the beads 8 have an increased radiopacity compared to the body of the stent, for instance by a factor of at least about 4.

The length of the stent in this condition is $L_2$ (not shown), whilst its diameter is $d_2$. The angle $\alpha_2$ between the filaments is reduced by 10 to 60% of the original angle. The stent can be retained in this condition either by exerting radial inwardly directed forces from the stent along its length, or by exerting axially outwardly directed forces at the ends of the stent. The fixing of the ends of the filaments according to the present invention render this latter means of retaining the -stent in its radially compressed condition more convenient since it can be achieved by extending pins or other means between the filaments adjacent to the bead 8, or beyond the first crossover points along the length of the stent, at each end and increasing the separation between the ends to extend to the stent in the axial direction.

As well as making it convenient to extend the stent, and stabilise it against flaring at the ends, the joining of the ends of the filaments allows the stent further to be axially compressed by exerting axially inwardly directed pressure against each end, so as to expand the radius of the stent, especially in its central portion, beyond the diameter $d_1$. The stent can thus be used to exert radially outwardly forces at a greater radial distance from the axis (than $d_1$) inside the blood vessel, for instance adding to or replacing the step of balloon dilatation prior to stent deployment. Without the joining of the filament ends such a step might be completely impossible and, even if it were, the stent ends would be damaged during such an operation. With the angle $\alpha$ being less than 90°, the use of the stent as a dilation device is convenient since a relatively large increase in diameter can be achieved with a relatively small axial reduction in length (as compared to a stent with a higher value of $\alpha$).

Figure 3:
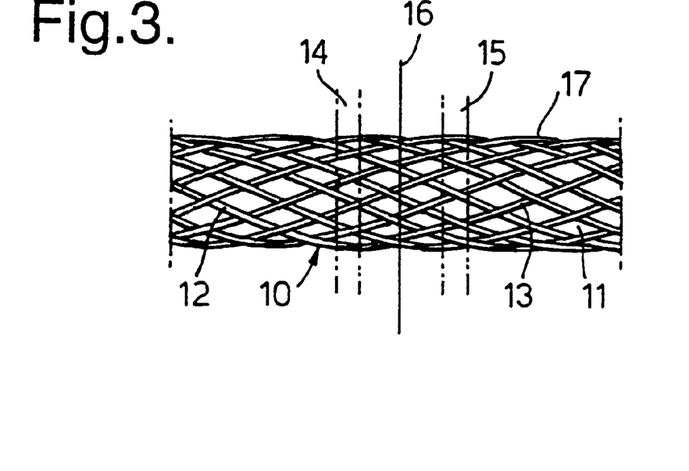
FIG. 3 shows a plan view of a portion of the first mandrel carrying a stent precursor during the execution of the method of the present invention.
Figure 4:
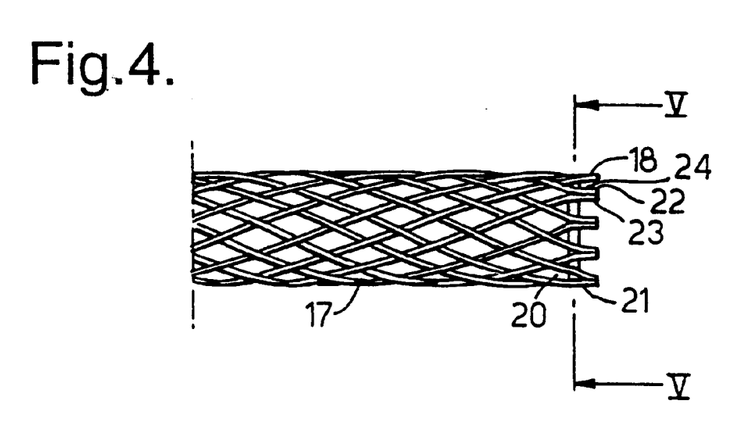
FIG. 4 shows in plan a portion of the second mandrel carrying a stent portion prior to joining of the filaments to one another.
Figure 5:
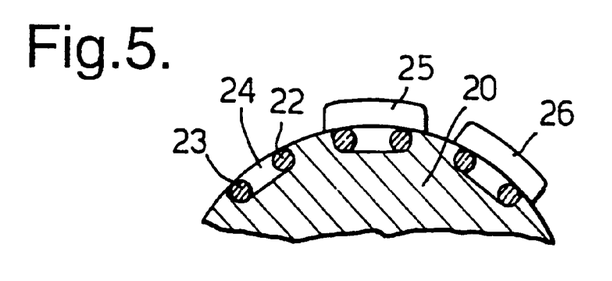
FIG. 5 is a partial section along line V—V of FIG. 4.

FIGS. 3 to 5 show how some of the steps of the method of the invention are carried out. In FIG. 3, a portion of a stent precursor which has been formed by braiding ten right handed helical filaments 12 and ten left handed helical filaments 13 all formed of high cobalt steel onto a mandrel 11. The filaments are again braided in a one over/one under pattern, by the following steps:

1. Wind the material from the supply spools onto the braiding bobbins.
2. Load the bobbins onto the braiding machine taking care to thread the tensioning system correctly.
3. Select the correct size of braiding mandrel (Dependant on the require stent size, usually 2 mm below the required diameter of stent i.e. for a 8 mm diameter stent use 6 mm mandrel).
4. Check the tension of each carrier and ensure that all carriers are of the same tension.
5. Secure all the ends of the wires onto the braid mandrel.
6. Set the haul off speed to obtain the correct braid angle.
7. Operate the machine to produce the desired amount of braid.
8. Secure the leading end of the braid onto the braiding mandrel using adhesive tape.
9. Slide a heat-treatment tube over the braid.
10. Trim a length of braid from around the heat-treatment mandrel allowing the braid to expand into the tube.
11. Remove the tube from braid mandrel making sure that the braid is secured on the inside of the tube.
12. Place both the tube and the braid into the shield box, taking care not to dislodge the braid from the inside of the tube.
13. Seal the box and purge using argon gas for a period of about 30 minutes.
14. Ensure that the oven is at 520° C.
15. Place the shield box into the oven whilst continuing to purge with argon although at a lower flow rate.
16. Monitor the temperature within the shield box via the data logger.
17. Once the internal temperature of the shield box has reached 520° C. allow the samples to dwell for a period of 3 hours.
18. After the 3 hours remove the shield box and allow to cool in air at ambient temperature.
19. Once cooled remove the tubes from the shield box and then remove the braid from the tubes.
20. Place the stent into the welding jig, trim the stent to the desired length before welding the ends.

A resistance welding technique with the welding device arranged in a ring around the stent precursor is used. This retains the filaments fixed relative to one another at these crossover points. Once secured, the wires are severed around the circumference at position 16, which is located midway between two series of crossover points. With the filaments secured at 15 and, though not shown, at the other, leading end of the stent portion 17, this can be removed from the mandrel 11.

As shown in FIG. 4, stent portion 17 is mounted onto a second mandrel 20 such that the ends 18 of the filaments extend beyond the end 21 of the mandrel. A pair of filaments 22, 23 is received in a pocket 24 formed in the surface at the end of the mandrel 20. As shown more clearly in FIG. 5 which is an expanded partial crosssection along line V—V of FIG. 4, the filaments 22 and 23 are positioned along the edges of the pocket 24 formed in the end of the mandrel 20.

Also shown in FIG. 5 are two components 25, 26 of a ring of heat sink components which are positioned across the filaments in the pockets and serve both to hold the filaments stationary and to conduct heat away from the filaments during the welding operation. The heat sink components are generally formed of copper. During the welding step, a plasma welding torch is directed at the ends 18 of the filaments extending beyond the end 21 of the mandrel shown in FIG. 4. The torch is directed at the ends for a time sufficient to fuse the metal of the filaments such that a globule of metal is formed. The heat sink components 25, 26 conduct heat away and, when the heat source is removed, the globules fuse to form metal beads 8 shown in FIG. 1.

During the welding step the filaments near to the beads 8 have been subjected to relatively high temperatures and, where the metal is high cobalt stainless steel, this affects the hardness of the material in the end portions of the stent. This differential hardness between the ends and the central portion of the stent may be disadvantageous and so the stent is annealed after the welding step and before removal from the mandrel 20 by heating at a temperature of 520° C. for 3–4 hours.

After the annealing step, the stent is coated with a solution of a 1:2 (mole) copolymer of (methacryloyloxy ethyl)-2-(trimethylammonium ethyl) phosphate inner salt with lauryl methacrylate in ethanol (as described in example 2 of WO-A-93/01221) as follows. The stent in relaxed form is placed in a tube having a slightly larger diameter than the stent. The tube is filled with coating solution and the solution is allowed to drain steadily from the tube to form a completely coated stent. Immediately thereafter a stream of warm air or nitrogen is directed through the tube at a linear velocity of 0.1–5 m/s at room temperature to 50° C. for a period of 30 seconds to 5 minutes to dry the coating by evaporation of the ethanol solvent.

Examination of the coating by scanning electron microscopy indicated that the coating substantially completely covered all the filaments, including the surfaces of the wires at the crossover points.

An alternative, cross-linkable coating consists of a polymer of 23 mole % (methacryloyloxy ethyl)-2-(trimethylammonium ethyl) phosphate inner salt, 47 mole % lauryl methacrylate, 5 mole % γtrimethoxysilylpropyl methacrylate and 25 mole % of γhydroxypropyl methacrylate. This is applied to the stent by the above described technique from a 5 mg/ml ethanolic solution. The solution is dried as described above and then cured by heating at 70 to 75° C. for a period of at least about 1 hour, for instance overnight. This curing results in substantially complete reaction of the methoxy silyl groups, either with other methoxysilyl groups or with hydroxy groups derived from the hydroxypropyl methacrylate monomer, driving off methanol. The coating, when observed by scanning electron microscope provides complete coverage of the filaments, no bridging at crossover points and is more resistant to damage at the crossover points than the above described two component copolymer.

The coated stent was sterilised by ethylene oxide, gamma radiation or electron beam and was subsequently mounted onto a standard delivery device as is used to deliver a Wallstent ready for deployment. The stent may alternatively be mounted onto the device on the distal end of which is illustrated in FIGS. 8 to 10.

Figure 6:
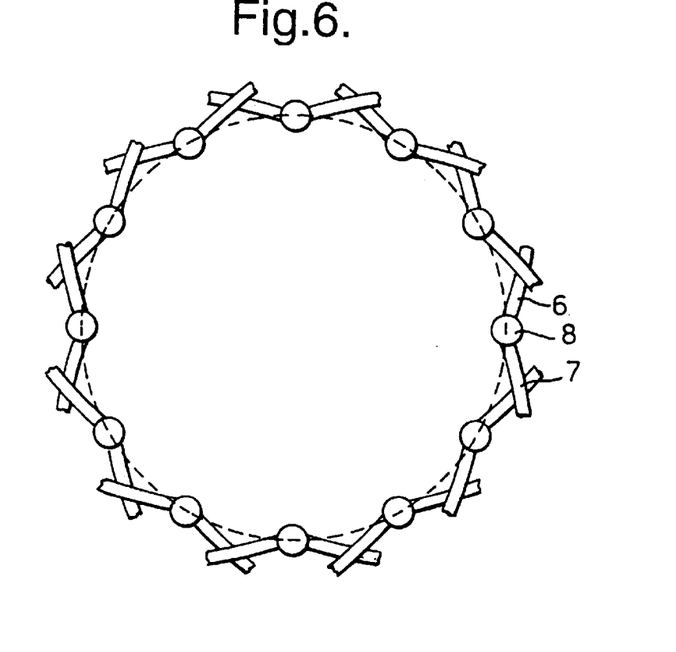
FIG. 6 is a partial end on view of another embodiment of a stent showing every pair of counter-rotating filaments welded.
Figure 7:
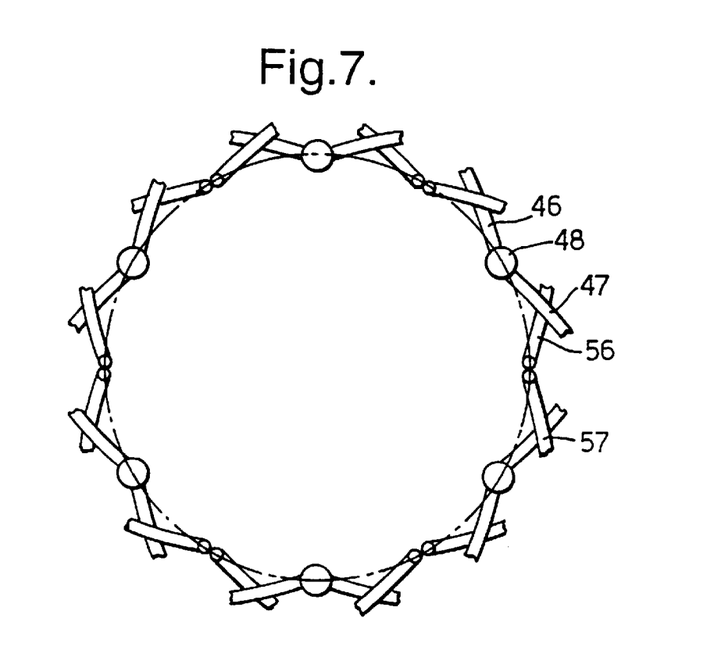
FIG. 7 is a partial end on view of an alternative stent to that of FIG. 6, in which every alternate pair of counter-rotating filaments is welded.

FIG. 6 shows an end on view of a further embodiment of the stent of the first aspect of the invention. This differs from the stent of FIGS. 1 to 5 since it consists of 12 filaments in each direction. The stent has been made by the same technique as described for FIG. 1 to 4. Thus each pair 6, 7 of counter-rotating filaments is welded together at a bead 8. FIG. 7 shows an alternative embodiment in which every alternate pair is welded. Thus counter-rotating filaments 46 and 47 are welded together at a bead 48, whilst counter-rotating helices 56 and 57 are not welded together. For some embodiments this gives adequate stability and allows convenient delivery means to be used whilst allowing control of mechanical characteristics by subjecting only half the filaments to the high welding temperatures.

Figure 8:
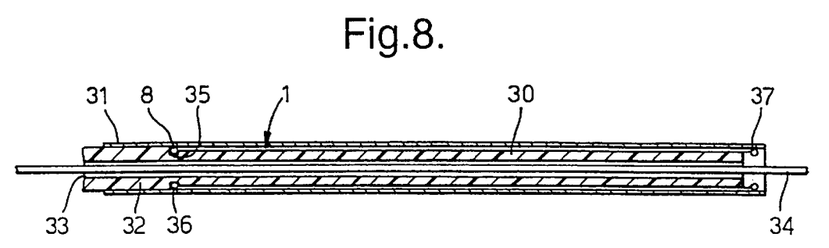
FIG. 8 is a section on an axial plane of a stent loaded in a delivery device in its radially compressed conformation.

As shown in FIG. 8, a stent 1 is retained in an annular space 30 between an external sleeve 31 and a pusher tube 32. The pusher tube 32 has a guidewire lumen 33 allowing passage therethrough of a guidewire 34. The pusher tube 32 has a circumferential groove 35 in its external wall having a depth and width (in the axial direction) of appropriate diameter for receipt of the beads 8 of the stent at its proximal end 36. The outer diameter of the pusher tube 32 distal from the groove 35 is preferably less than the outer diameter of the pusher tube proximal from the groove which in turn is dimensioned to allow a snug, sliding fit between the pusher tube and the outer sleeve 31. The reduced diameter portion distal from the groove 35 allows formation of the annular space 30 between the pusher tube 32 and the outer sleeve 31.

Figure 9:
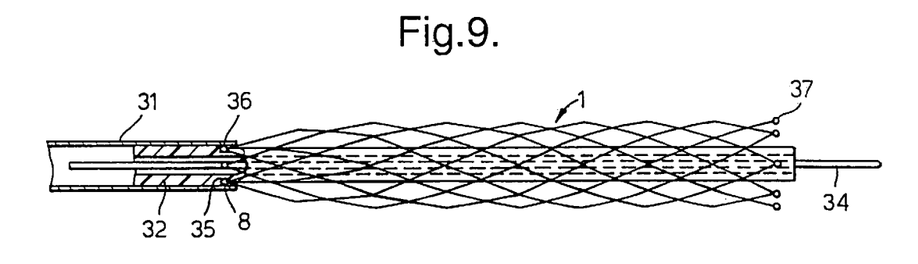
FIG. 9 shows the system of FIG. 8 with the stent partially deployed.
Figure 10:
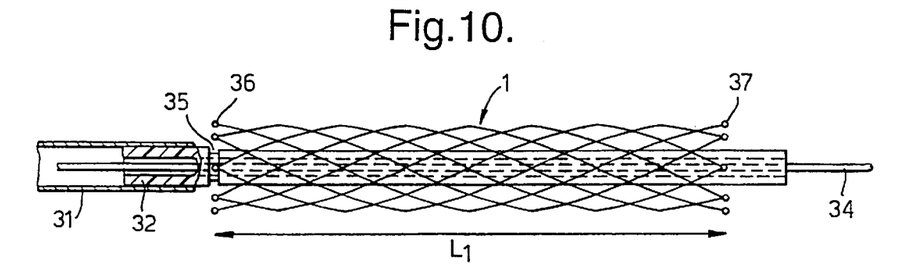
FIG. 10 shows the system of FIG. 8 with the stent fully deployed.

FIG. 9 shows the stent 1 partially deployed. The pusher tube 32 has been moved distally whilst the outer sleeve 31 has been moved axially in a proximal direction so that the sleeve has been retracted first from the distal end 37 from the stent until, as shown in FIG. 10, the proximal end of the stent is released from the groove 35. When the stent is partially deployed as shown in FIG. 9, it can be retracted into the delivery device by pulling pusher 32 back into the sleeve. Since the beads 8 at the proximal end 36 of the stent are fixed in groove 35 of the pusher, and since the distal wall of groove 35 bears against the shoulder provided by the distal edge of beads 8, the stent will be retracted back into the sleeve. The retraction may be partial, to make axial repositioning in a proximal direction less damaging on the internal wall of a vessel in which the stent is deployed. Alternatively the stent may be fully retracted to the position shown in FIG. 8 for complete removal from the vessel or repositioning.

As shown in FIG. 10, the stent is in its fully radially expanded configuration. The guidewire 34 remains in place. It can be seen that the length $L_1$ of the stent in the radially expanded configuration is less than the length in the radially compressed configuration shown in FIG. 8. A compensation mechanism could be provided whereby the distal end 37 of the stent remains in the same axial position in the vessel as the rest of the stent is deployed. The stent will not move axially relative to the vessel wall, thereby minimising damage during deployment.

Subsequently the pusher tube 32 will be pulled back to the sleeve 31 for retraction of the entire device along the guidewire and out of the patient.

Optionally after deployment of the self-expanding stent in a body vessel, it may be pushed against the internal vessel wall by a balloon catheter introduced via the guidewire until it is located within the stent. Alternatively, where the stent of the second aspect of the invention is used, the mechanically radially expanded stent which is formed of a shape memory alloy which changes shape or increases in hardness above a transition temperature, it may be desirable to provide means for heating the device to a temperature above the transition temperature of the alloy, where that temperature is above 37° C. For instance a balloon catheter provided with means for circulating heated fluid into the balloon is known and could be used.

While the invention has been described in detail and with reference to specific embodiments thereof, it will be apparent to one skilled in the art that various changes and modifications can be made therein without departing from the spirit and scope thereof.

What is claimed is:

1. A radially self-expanding stent adapted for implantation in a body passage comprises first and second sets of mutually counter-rotating metallic filaments which are braided together and define a tubular stent body having two ends which is biased towards a first radially expanded configuration in which it is unconstrained by external applied forces and can be retained in a second radially compressed configuration, in which in the said first configuration the angle α between the filaments at a crossover point at the mid point of the stent is less than 90° and in which some or all of the filaments at the ends of the body are fixed together in pairs each consisting of counter-rotating filaments such that the angle at which the filaments are fixed is within the range α−10 to α+10, and in which the filaments are joined at a bead which has a diameter of at least 1.2 times the diameter of the filament.

2. The stent according to claim 1 wherein α is in the range of 60° to 90°.

3. The stent according to claim 2 wherein the angle at which the filament ends are fixed is in the range of α−5 to α.

4. The stent according to claim 1, further comprising a polymeric biocompatible coating comprising a zwitterionic pendant group coating the surfaces of the filaments.

5. The stent according to claim 1, wherein the filaments are free to slide over each other at the crossover points.

6. The stent according to claim 1, wherein each beed has a diameter of more than twice the mean diameter of each filament.

7. The stent according to claim 1, wherein the filaments are formed of a shape memory alloy having a transition temperature and in which the stent adopts the said first radially expanded configuration below the transition temperature of the alloy and, when the stent is subjected to a temperature above the transition temperature of the alloy the stent adopts a maximally radially expanded configuration in which one or both of the diameter and resistance of the stent to radial compression is increased.

8. A method of making a stent according to claim 1, which comprises braiding filaments over a first mandrel to make an elongate precursor, severing a pre-selected length from the precursor, placing the severed portion onto a second mandrel which has a diameter which is within the range (0.8 to 1.25)×d (where d is the diameter of the stent in its radially expanded condition) such that one end of the braided portion extends beyond the end of the second mandrel and in the method the protruding ends of at least some of the filaments are joined to each other in counter-rotating pairs whereby each pair of counter-rotating filaments is joined by a beed of metal having a diameter of at least 1.2 times the mean diameter of the individual filaments.

9. The method according to claim 8, which comprises joining the filament ends together by welding.

10. The method according to claim 9, which comprises annealing the stent before or after the welding step.

11. The method according to claim 8, which comprises joining all the filaments required to be welded at one end of the stent in their respective pairs simultaneously and, in a separate step, joining all the filaments required to be welded at the other end in their respective pairs.

12. The method according to claim 8, which comprises subsequently coating the stent with a liquid coating composition and drying the coating to form an adherent coating of a biocompatible polymer.

13. The method according to claim 12, wherein the polymer comprises zwitterionic pendant groups.

14. The method according to claim 12, which comprises drying the coating by directing a flow of gas through the stent in an axial direction.

15. A graft comprising at least one stent according to claim 1 surrounded by a sleeve formed of an elastomeric material.

16. A combination of a stent according to claim 1, the stent being in the radially compressed configuration, and a delivery device, in which the delivery device comprises an internal pusher tube comprising an inner guidewire lumen for receiving a guidewire, and an external sleeve, the sleeve and pusher defining there between an annular space, wherein the stent is surrounded along substantially its entire axial length by the sleeve and at least one end of the stent is retained in the annular space between the sleeve and pusher.

17. The stent according to claim 1, wherein α is in the range of 65° to 85°.

18. The stent according to claim 1, wherein α is in the range of 70° to 80°.

19. The stent according to claim 4, wherein the polymeric biocompatible coating comprises an ammonium phosphate ester group.

* * * * *